US010704991B2

(12) United States Patent
Kei et al.

(10) Patent No.: US 10,704,991 B2
(45) Date of Patent: Jul. 7, 2020

(54) CELL ASPIRATION SUPPORT SYSTEM

(71) Applicant: Yokogawa Electric Corporation, Musashino-shi, Tokyo (JP)

(72) Inventors: Takayuki Kei, Musashino (JP); Hironori Takai, Musashino (JP)

(73) Assignee: Yokogawa Electric Coporation, Tokyo (JP)

( * ) Notice: Subject to any disclaimer, the term of this patent is extended or adjusted under 35 U.S.C. 154(b) by 4 days.

(21) Appl. No.: 16/058,191

(22) Filed: Aug. 8, 2018

(65) Prior Publication Data
US 2019/0049343 A1 Feb. 14, 2019

(30) Foreign Application Priority Data
Aug. 9, 2017 (JP) ................................ 2017-153825

(51) Int. Cl.
*G01N 1/04* (2006.01)
*G02B 21/32* (2006.01)
(Continued)

(52) U.S. Cl.
CPC .............. *G01N 1/04* (2013.01); *C12M 33/04* (2013.01); *C12M 47/04* (2013.01);
(Continued)

(58) Field of Classification Search
CPC .......... G01N 1/04; G01N 2035/00425; G01N 2035/00445; G01N 33/4833; G02B 21/32;
(Continued)

(56) References Cited

U.S. PATENT DOCUMENTS 4,865,986 A * 9/1989 Coy .......................... B01L 7/52
 435/285.1
5,106,584 A * 4/1992 Funakubo ............ G01N 35/028
 422/63
(Continued)

FOREIGN PATENT DOCUMENTS

EP 2 955 502 A1 12/2015
JP 60-46128 U 4/1985
(Continued)

OTHER PUBLICATIONS

Communication dated Dec. 12, 2018, issued by the European Patent Office in counterpart European Application No. 18187519.6.
(Continued)

*Primary Examiner* — Oschta I Montoya
(74) *Attorney, Agent, or Firm* — Sughrue Mion, PLLC

(57) ABSTRACT

A cell aspiration support system includes an image acquisition unit, an image processing unit, a display unit, an operation control unit and a cooling unit. The image acquisition unit acquires an image of the group of cells. The image processing unit identifies a cell from the acquired image to calculate feature quantities of each cell, and detects a cell whose feature quantities satisfy predetermined conditions. The display unit displays information relating to the group of cells in a state in which the detected cell is distinguishable. When receiving designation of the specific cell based on the information, the operation control unit moves the cell culture container such that a specific cell is placed at a predetermined aspiration position and moves an aspiration tip to the aspiration position. The cooling unit holds a specimen rack storing an aspirated tip after aspiration and cools the tip.

7 Claims, 9 Drawing Sheets

(51) Int. Cl.
  *C12M 1/00*    (2006.01)
  *C12M 1/26*    (2006.01)
  *G01N 33/483*  (2006.01)
  *G02B 21/36*   (2006.01)
  *G06K 9/00*    (2006.01)
  *G01N 35/00*   (2006.01)
  *G02B 21/00*   (2006.01)
  *G02B 21/12*   (2006.01)
  *G02B 21/26*   (2006.01)

(52) U.S. Cl.
  CPC ......... *G01N 33/4833* (2013.01); *G02B 21/32* (2013.01); *G02B 21/365* (2013.01); *G06K 9/0014* (2013.01); *G06K 9/00134* (2013.01); *G01N 2035/00425* (2013.01); *G01N 2035/00445* (2013.01); *G02B 21/0076* (2013.01); *G02B 21/12* (2013.01); *G02B 21/26* (2013.01)

(58) Field of Classification Search
  CPC .. G02B 21/365; G02B 21/0076; G02B 21/12; G02B 21/26; G06K 9/00134; G06K 9/0014; C12M 33/04; C12M 47/04
  See application file for complete search history.

(56) References Cited

U.S. PATENT DOCUMENTS

| | | |
|---|---|---|
| 2009/0098593 A1 | 4/2009 | Ehrhardt et al. |
| 2013/0240181 A1 | 9/2013 | Yasunaga |
| 2015/0362716 A1 | 12/2015 | Kei et al. |

FOREIGN PATENT DOCUMENTS

| | | |
|---|---|---|
| JP | 61-4745 U | 1/1986 |
| JP | 4-88843 U | 8/1992 |
| JP | 2013-190245 A | 9/2013 |
| JP | 2016-7 A | 1/2016 |
| WO | 2013/019491 A1 | 2/2013 |

OTHER PUBLICATIONS

Gyorgy Hegyi et al : "Storage of biological samples", Dec. 31, 2013, Introduction to Practical Biochemistry, XP055530543, (pp. 18-20).

* cited by examiner

FIG. 5A
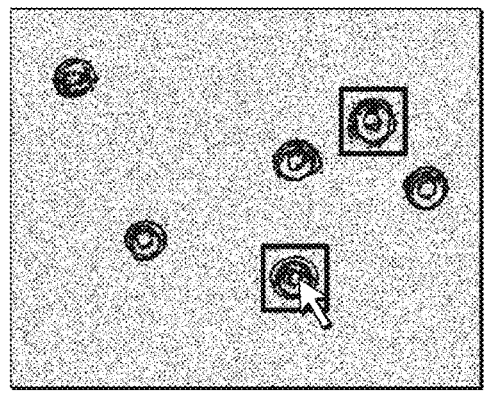
FIG. 5B
| IDENTI-FIER | POSI-TION | SIZE | LUMI-NANCE#1 | LUMI-NANCE#2 | ... |
|---|---|---|---|---|---|
| aaa | xaa yaa | a111 | a112 | a113 | ... |
| bbb | xbb ybb | b111 | b112 | b113 | ... |
| ccc | xcc ycc | c111 | c112 | c113 | ... |
| ddd | xdd ydd | d111 | d112 | d113 | ... |
| eee | xee yee | e111 | e112 | e113 | ... |
| ⋮ | ⋮ | ⋮ | ⋮ | ⋮ | |
FIG. 5C
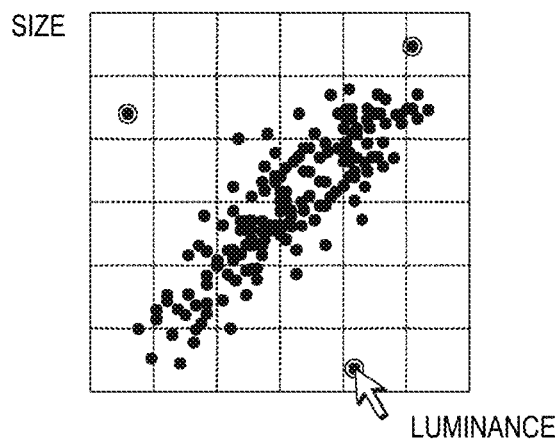

330

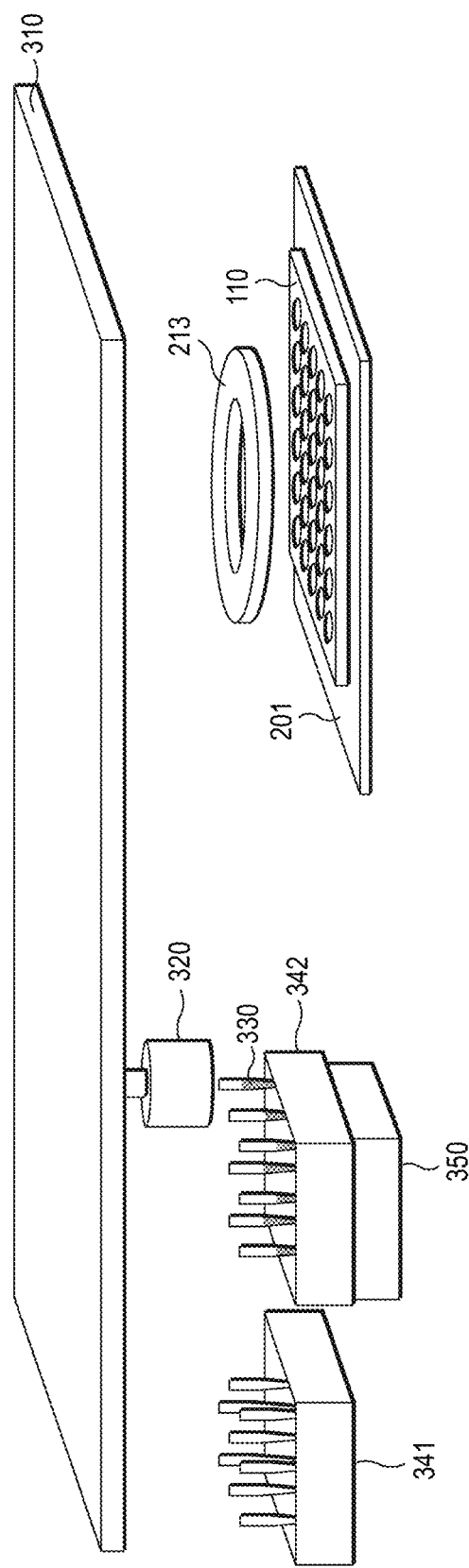

CELL ASPIRATION SUPPORT SYSTEM

CROSS-REFERENCE TO RELATED APPLICATION

The present application claims priority from Japanese Patent Application No. 2017-153825 filed on Aug. 9, 2017, the entire content of which is incorporated herein by reference.

BACKGROUND

Technical Field

The present invention relates to a cell aspiration support system which supports aspiration operation of cells or cell components, and particularly relates to a cell aspiration support system suitable for aspiration operation targeting a large number of cells.

Related Art

In a study and the like of a life system, characteristic cells are specified from many cells in cell culture wells, and operation of aspirating the cells or components of the cells is frequently performed. For example, in a drug discovery process of discovering or designing a new drug, a drug discovery screening stage of finding out a candidate compound showing drug efficacy/activity from many candidate compounds is performed. In this stage, cells showing a remarkably specific change are selected from a group of cells in the cell culture wells to which the candidate compound is provided, the cells or cell components are aspirated, and analysis such as mass spectrometry is performed.

When aspirating the cells, cell aspiration operation is performed while a cell to be aspirated is confirmed with a microscope using an aspiration pipette or a dispensing device equipped with an aspiration tip. When aspirating the cell components, cell aspiration operation is performed while a cell to be aspirated is confirmed with a microscope using a fine tip called a nanospray tip.

In operation of aspirating cells or cell components, Cells to be analyzed are selected and aspirated and aspiration is performed while visually observing individual cells. So, it is very troublesome to process a large number of cells, and a burden on an operator is big. In order to reduce the burden, JP-A-2016-000007 discloses a cell aspiration support system that easily detects a candidate cell to be analyzed from a large number of cells and can perform aspiration operation immediately.

SUMMARY

In a specimen having aspirated cells or cell components, since an enzymatic reaction is easy to occur at room temperature, properties of protein at the time of aspiration and properties of protein after storage at room temperature for a while are different in some cases. When such an enzymatic reaction proceeds, it is concerned that accuracy of results of mass spectrometry is adversely affected.

Therefore, an object of the present invention is to be able to maintain properties of a specimen at the time of aspiration in a cell aspiration support system that supports aspiration operation targeting characteristic cells in a large number of cells.

In order to solve the above problems, a cell aspiration support system of the present invention which supports operation of aspirating a specific cell or cell component, from a group of cells in a cell culture container, includes an image acquisition unit, an image processing unit, a display unit, an operation control unit and a cooling unit. The image acquisition unit acquires a microscopic image of the group of cells. The image processing unit identifies a cell from the acquired image to calculate feature quantities of each cell, and detects a cell whose feature quantities satisfy predetermined conditions. The display unit displays information relating to the group of cells in a state in which the detected cell is distinguishable. When receiving designation of the specific cell based on the information relating to the group of cells, the operation control unit moves the cell culture container such that a specific cell is placed at a predetermined aspiration position and moves an aspiration tip to the aspiration position. The cooling unit holds a specimen rack storing an aspirated tip after aspiration and cools the tip.

Here, the cooling unit may include a cooler that uses a Peltier element, and a heat transfer member that contacts with the cooler and includes holes containing tip ends of the tips.

In addition, the cooling unit may include an opening-and-closing type heat insulation cover that is opened when the aspirated tip after aspiration is stored in the specimen rack.

The cooling unit may surround the specimen rack. The heat transfer member may contact with a cooling side of the cooler and a heat sink may be provided on a heat exhaust side of the cooler. The heat insulation member may surround the cooler and the heat transfer member. The opening-and-closing type heat insulation cover may open and close along with movement of the aspiration tip.

According to the present invention, in the cell aspiration support system that supports aspiration operation targeting characteristic cells in a large number of cells, it is possible to maintain properties of the specimen at the time of aspiration.

BRIEF DESCRIPTION OF THE DRAWINGS

FIGS. 5A, 5B and 5C show display examples of an analysis result.

FIG. 9 illustrates moving operation of the aspiration unit after cell aspiration.

DETAILED DESCRIPTION

Figure 1:
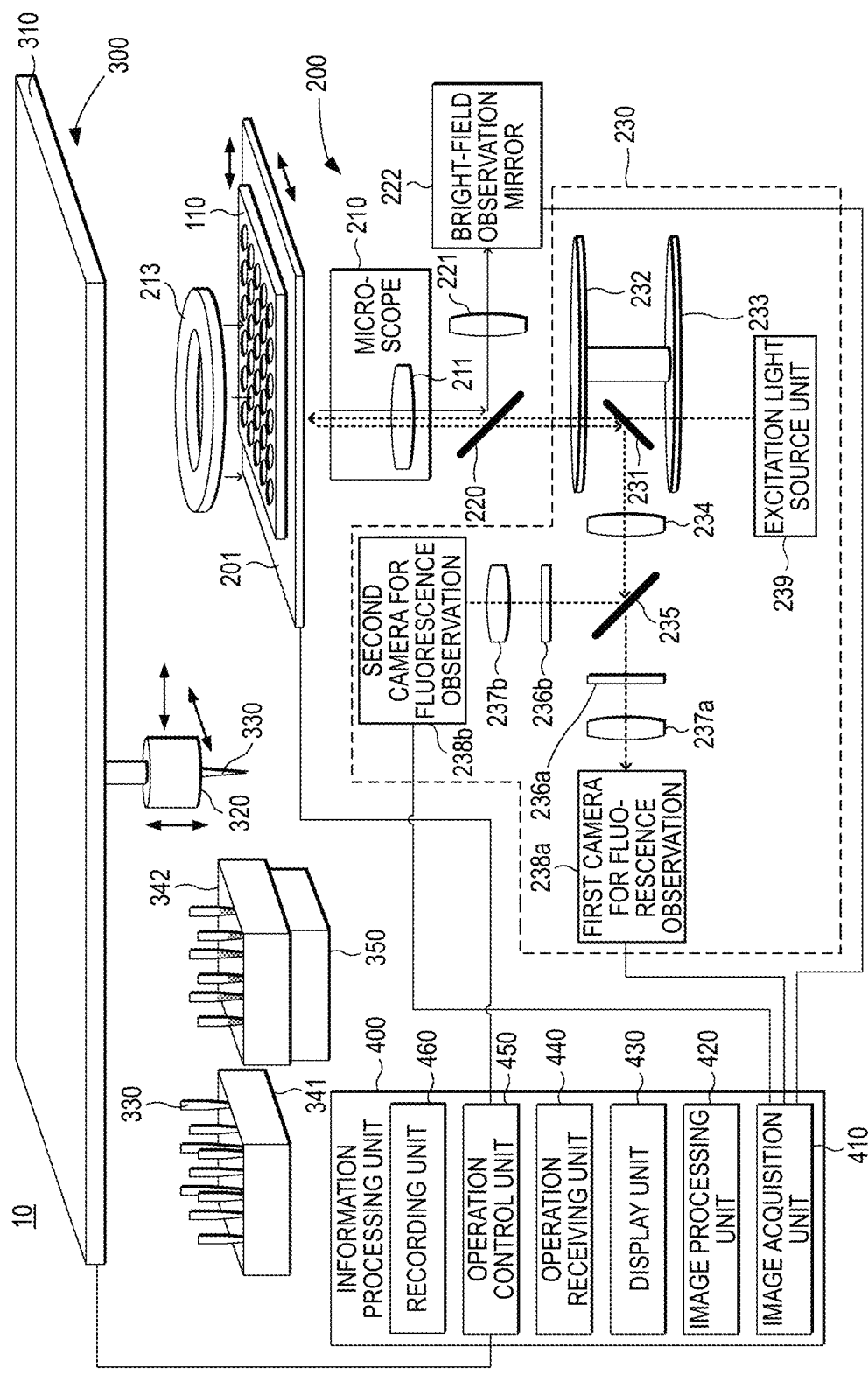
FIG. 1 shows a configuration of a cell aspiration support system according to the present embodiment.

An embodiment of the present invention will be described with reference to the drawings. FIG. 1 shows a configuration of a cell aspiration support system according to the present embodiment. The cell aspiration support system 10 is an apparatus that supports aspiration process of cells or cell components, and includes an optical system unit 200, an aspiration operation unit 300, and an information processing unit 400. Hereinafter, unless particularly distinguished, cell aspiration is not only aspiration of one cell, but includes aspiration of cell components such as small organs in cells.

The optical system unit 200 includes an XY stage 201 carrying a microplate 110 on which a plurality of wells are formed, a microscope 210 including an objective lens 211, a bright-field illumination 213, a dichroic mirror 220, a variable power lens 221, a bright-field observation camera 222, and a confocal scanner unit 230.

Additionally, a cell culture container may be carried on the XY stage 201. The present invention is not limited to the microplate 110, but may be a cell culture dish, a cover glass chamber, a petri dish, or the like.

In the present embodiment, the optical system unit 200 will be described as an example of a configuration that performs confocal two-color fluorescence observation and bright-field observation, but the optical system unit 200 is not limited to this configuration. For example, the confocal scanner unit 230 or the bright-field observation system may be omitted to form a vertical fluorescence one-color configuration, a confocal one-color configuration, a confocal one-color and bright-field configuration, or the like.

The confocal scanner unit 230 includes a dichroic mirror 231, a pinhole array disc (Nipkow disc) 232, a micro lens array disc 233, a relay lens 234, a dichroic mirror 235, a first bandpass filter 236a, a first lens 237a, a first camera for fluorescence observation 238a, a second bandpass filter 236b, a second lens 237b, a second camera for fluorescence observation 238b, and an excitation light source unit 239.

In bright-field observation, the bright-field illumination 213 is irradiated toward the microplate 110. The bright-field signal light passes through the microscope 210 and is reflected by the dichroic mirror 220, and forms an image on the bright-field observation camera 222 by the variable power lens 221. In the bright-field illumination 213, a space is formed in the central portion, and is, for example, an annular shape (a doughnut shape).

In the fluorescence observation, an excitation light beam having a specific wavelength is emitted from the excitation light source unit 239 toward the microplate 110. A fluorescence signal having a wavelength longer than the excitation light beam is emitted from an excited sample, and the fluorescence signal having passed through the pinhole array disc 232 becomes a confocal image. The fluorescence signal is reflected by the dichroic mirror 231 and forms an image on the first camera for fluorescence observation 238a and the second camera for fluorescence observation 238b through the relay lens 234.

In order to correspond to simultaneous use of excitation light sources having plural wavelengths, the dichroic mirror 235 having a characteristic of dispersing a fluorescent signal is provided. Further, the first bandpass filter 236a and the second bandpass filter 236b are provided in order to improve an S/N ratio of an image and pass only necessary wavelength bands of the fluorescence signal. The fluorescence wavelength emitted from the sample is various. For example, it is desirable to prepare a plurality of bandpass filters 236 corresponding to necessary wavelengths using a filter foil or the like.

The aspiration operation unit 300 includes an XYZ stage 310, an aspiration unit 320, a tip rack 341, a specimen rack 342, and a cooling unit 350. A plurality of tips 330 for aspirating cells or cell components are arranged in the tip rack 341. The tips 330 which have aspirated cells or cell components are stored in the specimen rack 342. In the present embodiment, the specimen rack 342 is held in the cooling unit 350.

The aspiration unit 320 moves in directions of X axis, Y axis, and Z axis by the XYZ stage. When aspiration operation of cells is performed, the aspiration unit 320 acquires and mounts the tips 330 from the tip rack 341. Then, the aspiration unit 320 moves toward the microplate 110 and aspirates cells from wells at predetermined aspiration positions. The aspiration position can be, for example, on an optical axis of the microscope 210.

At this time, the XY stage 201 moves the microplate 110 such that the cells to be aspirated are positioned at the aspiration positions. Therefore, the tips 330 and the cells to be aspirated overlap vertically. Additionally, the bright-field illumination 213 is an annular so as not to interfere with the aspiration unit 320 during aspiration operation.

Figure 2:
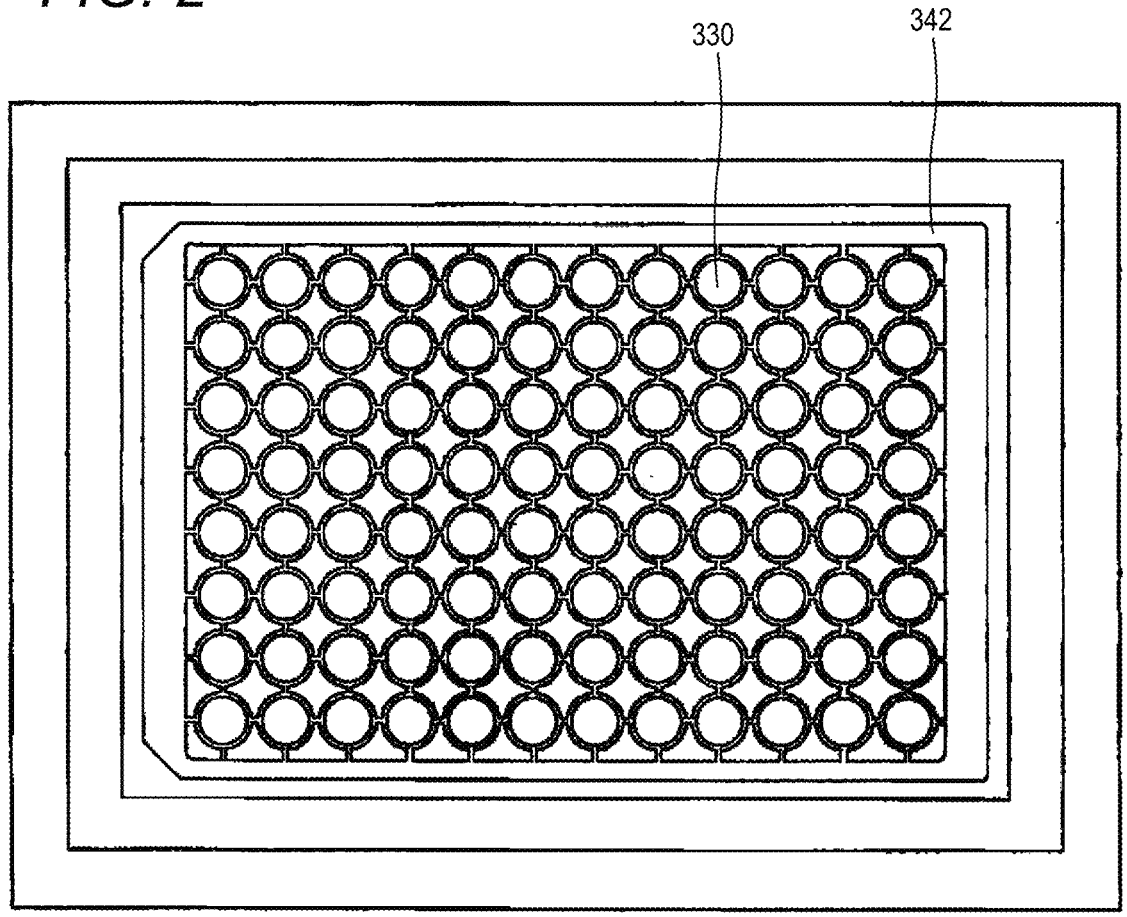
FIG. 2 shows a 96-well-type specimen rack.

After aspiration of the cells, the aspiration unit 320 moves toward the specimen rack 342, and releases and stores the cell-aspirated tips 330. The specimen rack 342 storing the cell-aspirated tips 330 can, for example, correspond to a format defined by ANSIUSLAS1-2004, which is the de facto standard of the drug discovery field. FIG. 2 shows a 96-well-type specimen rack 342 as an example.

Figure 3:
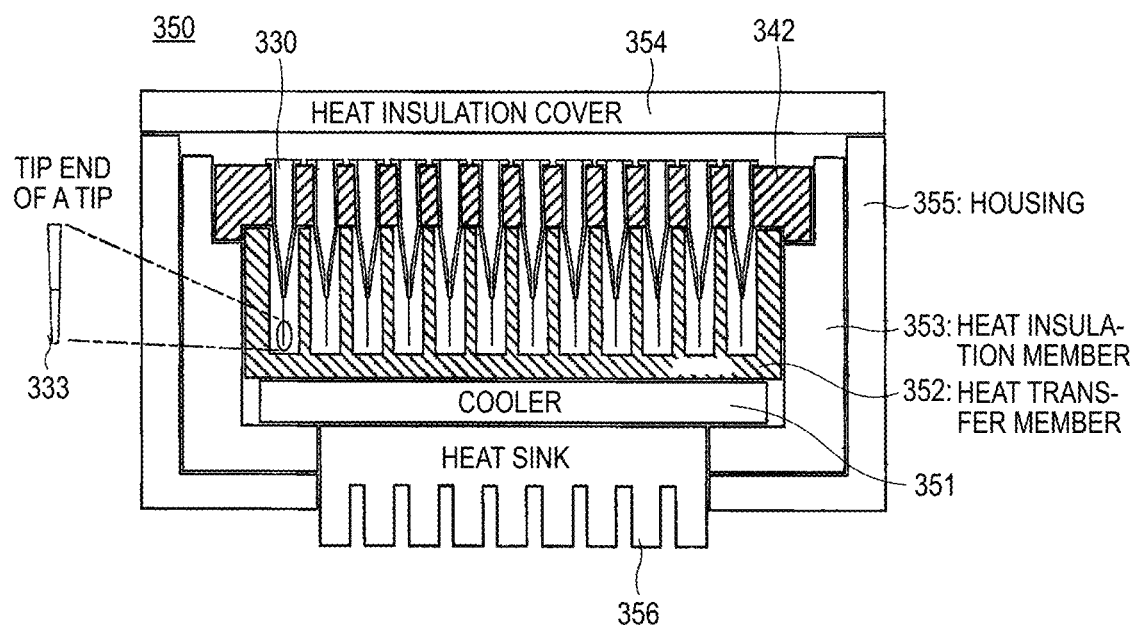
FIG. 3 shows a configuration of a cooling unit.

FIG. 3 shows the cooling unit 350 that holds the sample rack 342. The cooling unit 350 is shaped so as to surround the specimen rack 342 and includes a cooler 351 for cooling the tip 330 containing a specimen 333 at the tip end.

The cooler 351, for example, can suitably use a general Peltier element. In order to efficiently cool the specimen 333, a heat transfer member 352 is used, which is formed by a material such as aluminum having a good thermal conductivity. The heat transfer member 352 is formed such that 96 wells are provided corresponding to the 96-well-type specimen rack 342, and the specimen 333 at the tip end of the tip 330 enters into each well, and the heat transfer member 352 contacts with a cooling side of the cooler 351. On the other hand, a heat sink 356 is provided on a heat exhaust side of the cooler 351.

In order to isolate the cooler 351 and the heat transfer member 352 from surroundings, the cooler 351 and the heat transfer member 352 are surrounded by the heat insulation member 353, and a movable heat insulation cover 354 is provided on the upper portion of the cooling unit 350. The heat insulation cover 354 opens and closes by a driving mechanism (not shown) along with movement of the aspiration unit 320. That is, the heat insulation cover 354 is generally in a closed state, and opens when storing the cell-aspirated tips 330.

A housing 355 supports respective components of the cooler 351, the heat transfer member 352, the heat insulation member 353, the heat insulation cover 354, and the heat sink 356, and is contained in the cell aspiration support system 10 in a state of holding the specimen rack 342. When using the cell aspiration support system 10, the cooler 351 including a Peltier element or the like is energized, and the specimen 333 is cooled to a preset cooling temperature. For example, when the cooling temperature was set to −10° C., it is confirmed to reach a target temperature in about 5 minutes after the start of cooling.

In this way, in the present embodiment, since the specimen rack 342 is held and the cooling unit 350 for cooling the tip 330 is provided, it is possible to stop an enzymatic reaction of the specimen and maintain properties of the specimen at the time of aspiration. This makes it possible to maintain accuracy of analysis results of post-processes such as mass spectrometry.

The information processing unit 400 can be configured using an information processing device such as a PC and includes an image acquisition unit 410, an image processing unit 420, a display unit 430, an operation receiving unit 440, an operation control unit 450, and a recording unit 460. The image acquisition unit 410 acquires images from the bright-field observation camera 222, the first camera for fluorescence observation 238a, and the second camera for fluorescence observation 238b.

The image processing unit 420 performs image processing on the images acquired by the image acquisition unit 410, and then performs various analyses. Specifically, cells and cell organs are recognized by template matching or the like, and feature quantities such as size, luminance, protein amount, and ion amount of each identified cell are calculated. Also, processes such as listing, graphing, and the like of information relating to cells are performed using the calculated feature quantities.

The display unit 430 displays the image acquired by the image acquisition unit 410 and the analysis result of the image processing unit 420. The operation receiving unit 440 receives various operations from an operator.

The operation control unit 450 controls operation of the XY stage 201 and the XYZ stage 310, and moves the microplate 110 and the aspiration unit 320. The recording unit 460 records the image acquired by the image acquisition unit 410, the analysis result of the image processing unit 420, and the like.

Next, operation of the cell aspiration system 10 will be described with reference to the flow chart of FIG. 4. Additionally, the operation described below is an example, and the cell aspiration support system 10 can perform cell aspiration operation in various orders according to analytical policy of the operator, and the like.

First, the cell aspiration support system 10 receives a set of specimens and the like necessary for analysis from the operator (S101). That is, the operator sets the microplate 110 where the cells are cultured, at a predetermined position of the cell aspiration support system 10. At this time, fluorescent dyeing is performed as necessary. Further, the tip 330 according to the purpose of aspiration is placed on the tip rack 341. For example, when aspiration of cell components is performed, a nanospray tip is placed, and when aspiration of one cell is performed, a usual aspiration tip is placed.

Next, imaging conditions and the like are received from the operator via the operation receiving unit 440 (S102), and analysis contents and the like are received (S103). When receiving the imaging conditions, the cell aspiration is support system 10, for example, designates of an optical system such as a confocal point, vertical fluorescence, and phase difference, sets wavelength, and sets capturing interval/total capturing time and the like. By designating the confocal point, selection of three-dimensional components becomes easy during cell aspiration.

When receiving the analysis contents, calculation targets of the feature quantities, and detection conditions of cells of interest are set. The feature quantities can include luminance, size, and the like. When setting the detection conditions, a threshold value and the like of the feature quantities can be set, and cells satisfying the detection conditions are automatically detected.

Then, setting of an imaging range is received (S104), and imaging is executed by the bright-field observation camera 222, the first camera for fluorescence observation 238a and the second camera for fluorescence observation 238b (S105). A part of the cameras may be used.

When imaging, the image acquisition unit 410 acquires an image, and the image processing unit 420 performs analysis by image processing (S106). In analysis by image processing, cells satisfying extraction conditions are detected. Then, the display unit 430 displays the analysis result (S107). When displaying the analysis result, cells satisfying the detection conditions are made clear.

Specifically, for example, as shown in FIG. 5A, it is possible to clearly show the cells satisfying the detection conditions in an microscopic image. Further, as shown in FIG. 5B, it is also possible to list recognized cells and highlight cells satisfying the detection conditions. Furthermore, as shown in FIG. 5C, it is also possible to display a scatter diagram based on feature quantities of the recognized cells. In an example of this figure, a scatter diagram is drawn with size and luminance as axes, and cells satisfying the detection conditions are highlighted. Display of the analysis result is not limited to these examples, but various forms can be adopted.

The operator can designate a specific cell as an aspiration target with respect to the analysis result. Designation of the aspiration target may be performed on any cell, and the detected cells may be automatically designated in order.

When the operator designates any cell, for example, a cell to be aspirated may be clicked on the microscope image shown in FIGS. 5A to 5C. In the image processing unit 420, since each cell is identified, when a specific cell is designated in a display image, the cell in the microplate 110 can be specified.

Figure 4:
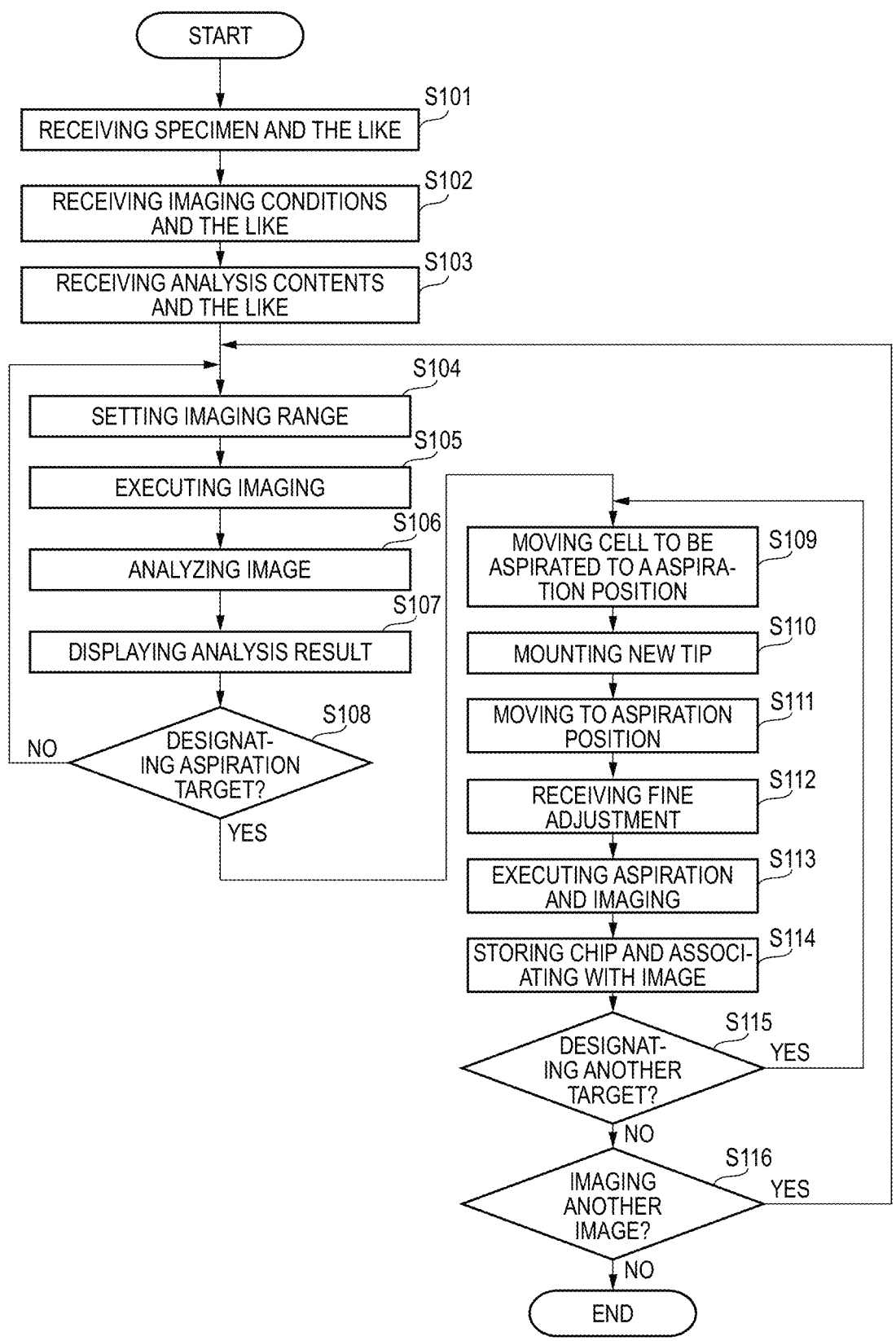
FIG. 4 is a flow chart illustrating operation of the cell aspiration support system.

Returning to description of the flowchart of FIG. 4, when a cell to be aspirated is not designated (S108: No), the imaging range is set again (S104), and subsequent processes are repeated.

When the cell to be aspirated is designated (S108: Yes), the operation control unit 450 controls the XY stage 201 and moves the cell to be aspirated to an aspiration position (S109). The aspiration position is, for example, on an optical axis of the microscope 210.

Figure 6:
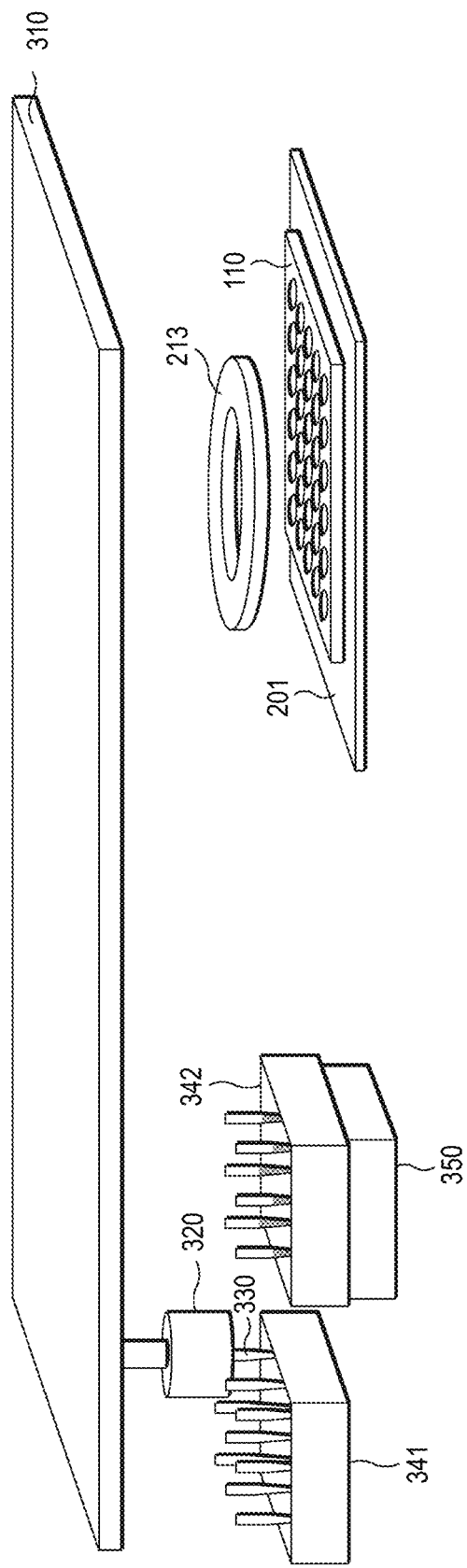
FIG. 6 illustrates moving operation of an aspiration unit before cell aspiration.

Further, the XYZ stage 310 is controlled, as shown in FIG. 6, the aspiration unit 320 is moved toward the tip rack 341, and a new tip 330 is mounted on the aspiration unit 320 (S110). Additionally, in this figure and in FIG. 7 to be described below, the specimen rack 342 is exposed, but actually, the heat insulation cover 354 of the cooling unit 350 is kept closed.

Figure 7:
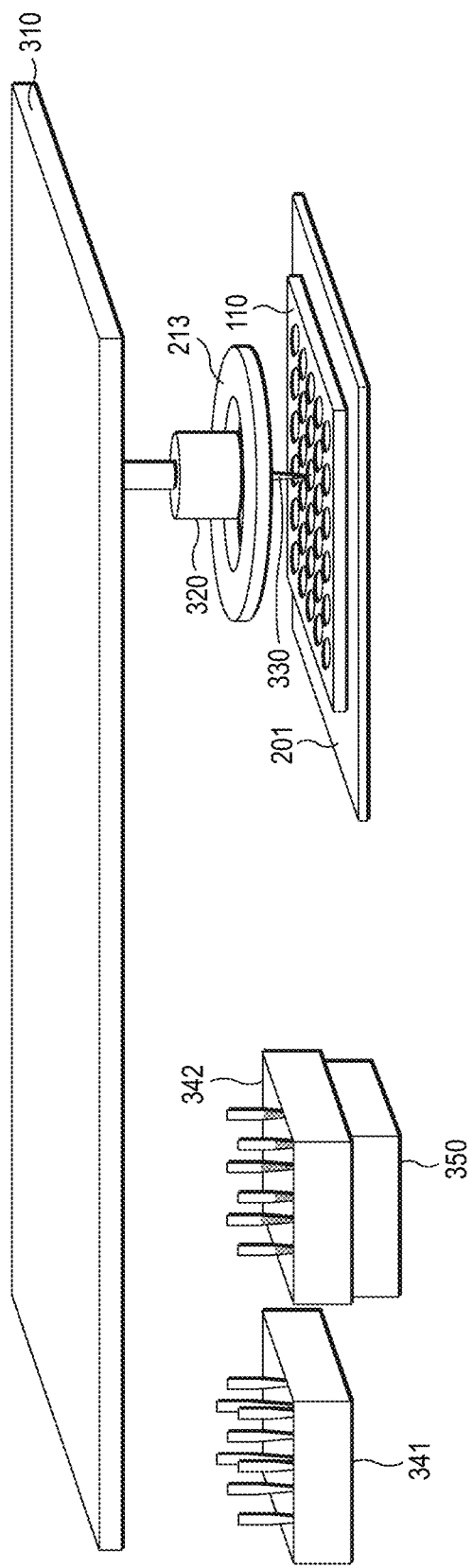
FIG. 7 illustrates moving operation of the aspiration unit and a microplate during cell aspiration.

Then, the XYZ stage 310 is controlled, and as shown in FIG. 7, the aspiration unit 320 is moved such that the tip 330 conforms to the aspiration position (S111). At this time, since the center of the bright-field illumination 213 is a space, the bright-field illumination 213 does not interfere with the aspiration unit 320.

As a result of processing (S110) and processing (S111), the cell to be aspirated and the tip 330 overlap vertically at the aspiration position. Therefore, it is possible to easily aspirate the cell to be aspirated. There are also cases where cells move from the time of image acquisition and there are also cases where a specific organ in a cell is to be aspirated. In these cases, fine adjustment of a position of the aspiration unit 320 or the microplate 110 can be received (S112) from the operator. At these times, adjustment of the aspiration unit 320 in a direction of Z axis may also be received.

Figure 8:
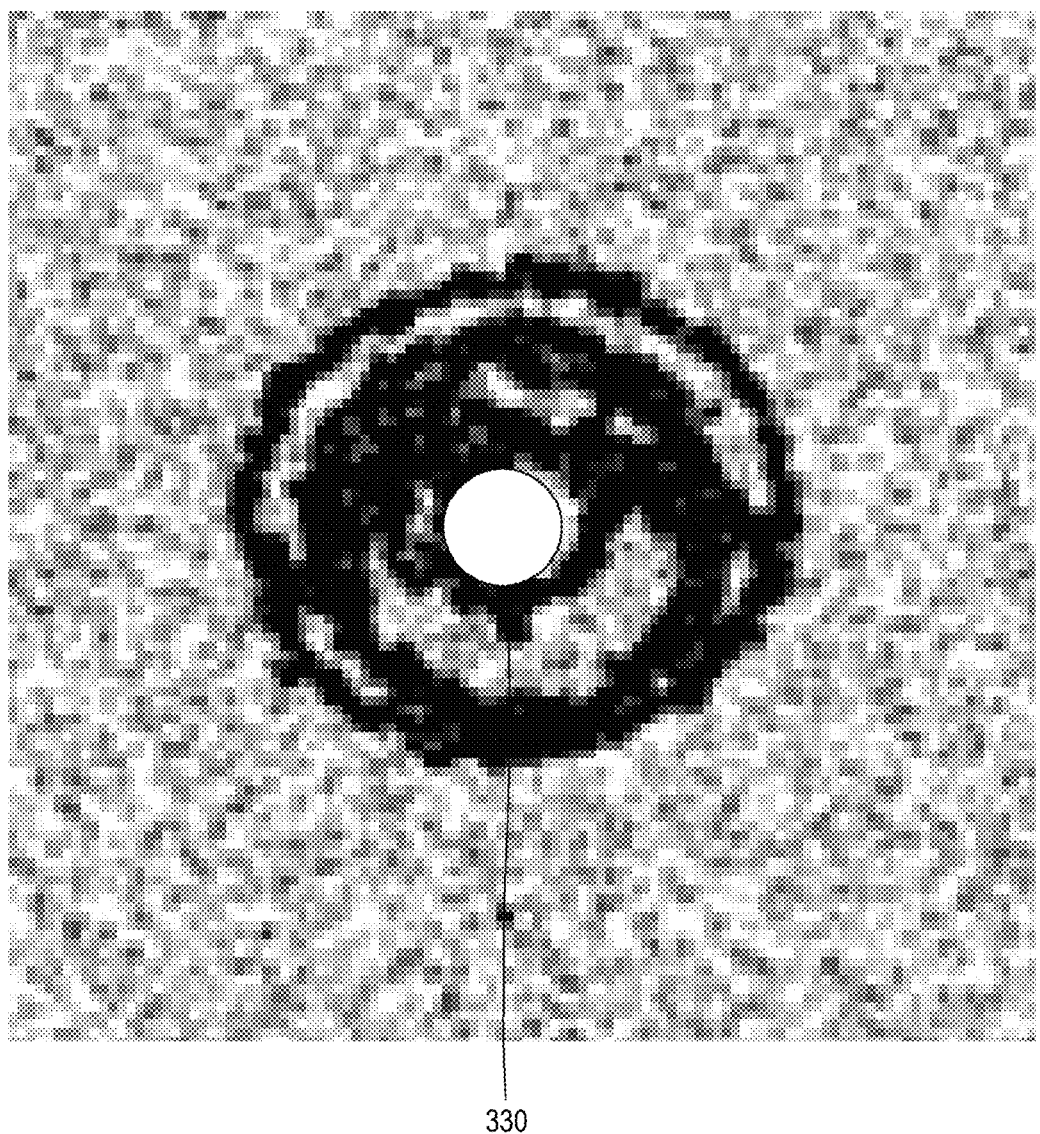
FIG. 8 illustrates fine adjustment of a tip position during cell aspiration.

In the fine adjustment of the position, as shown in FIG. 8, the microscopic image can be displayed on the display unit 430 in real time, and movement instructions can be received from the operator via the operation receiving unit 440. At this time, it is desirable to apply a fluorescent substance to the tip end of the tip 330, so that the position of the tip 330 can be grasped even in the fluorescence observation image. Alternatively, the tip 330 may be visualized by providing an LED light source in the vicinity of a tip mounting portion of the aspiration unit 320 and irradiating the tip 330 in the tip end direction with light having a predetermined wavelength.

When the fine adjustment of the position is finished, aspiration of cells is executed (S113). At this time, images before and after cell aspiration are imaged. Accordingly, certainty of the aspiration operation can be confirmed afterward.

After the aspiration of cells, as shown in FIG. 9, the operation control unit 450 controls the XYZ stage 310, the aspiration unit 320 is moved toward the specimen rack 342, and the cell-aspirated tip 330 is released and kept in the specimen rack 342 (S114). Only during this operation, the heat insulation cover 354 of the cooling unit 350 is opened and closed after the release.

After the release, since the cell-aspirated tip 330 is cooled by the cooling unit 350 that holds the specimen rack 342, properties of the specimen at the time of aspiration can be maintained. In addition, the recording unit 460 records the image imaged during the aspiration operation in association with the cell-aspirated tip 330.

If there are instructions to suck other cells in the image imaged in a processing (S105) (S115: Yes), a processing (S109) of moving the cells to the aspiration position and later processes are repeated.

If there is no instruction to aspirate other cells in the image imaged in the processing (S105) (S115: No), in a case where yet another image is imaged and the aspiration operation is continued (S116: Yes), a processing (S104) of setting the imaging range and later processes are repeated. On the other hand, in a case where another image is not imaged (S116: No), the aspiration operation is finished.

As described above, in the cell aspiration support system 10 of the present embodiment, cells are imaged, characteristic cells are detected by image processing, and a series of operations for moving the cells to be aspirated to the aspiration position are performed. Accordingly, the system reduces is workload of the operator which performs aspiration operation targeting characteristic cells in a large number of cells.

In addition, since the cell aspiration support system 10 provides with the cooling unit 350 which holds the specimen rack 342 and which cools the tip 330, an enzymatic reaction of the specimen can be stopped and properties of the specimen at the time of aspiration can be maintained. This makes it possible to maintain accuracy of analysis results of post-processes such as mass spectrometry.

Figure 10A:
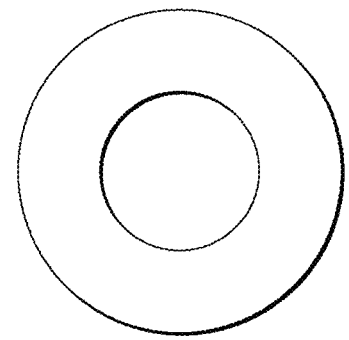
FIGS. 10A, 10B, 10C and 10D illustrate shape examples of a bright-field illumination.
Figure 10B:
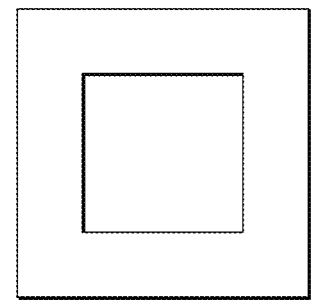
Figure 10C:
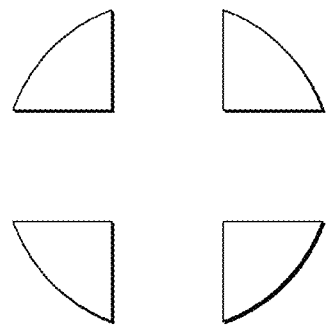
Figure 10D:
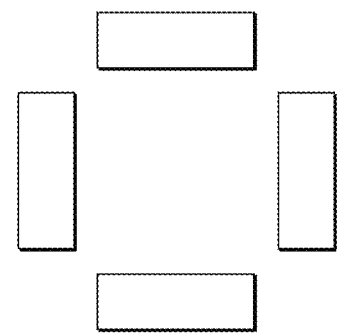

In the aspiration operation by the cell aspiration support system 10, in addition to aspiration of one cell, it is also possible to aspirate a specific cell component by using a nanospray tip as the tip 330. In this case, mass spectrometry can be performed with high sensitivity. In addition, when one cell is to be aspirated, process such as separation, selection, and removal of cells from a large number of cells can also be performed by selecting a specific cell, and application in the field of regenerative medicine and the like can be expected, As described above, the center of the bright-field illumination 213 is a space so as not to interfere with the aspiration unit 320 at the time of cell aspiration. The bright-field illumination 213 is not limited to an annular shape (donut-shape) as shown in FIG. 10A as long as the central portion is a space, but may be, for example, a rectangular frame as shown in FIG. 10B. Further, FIG. 10C and FIG. 10D may show a shape divided into a plurality of parts.

What is claimed is:

1. A cell aspiration support system comprising:
a personal computer (PC) configured to:
acquire a microscopic image of a group of cells;
identify a cell from the acquired image to calculate feature quantities of each cell, and detect a cell whose feature quantities satisfy predetermined conditions;
display information relating to the group of cells in a state in which the detected cell is distinguishable; and
when receiving a designation of a specific cell based on the information relating to the group of cells, move a cell culture container such that the specific cell is placed at an aspiration position and move an aspiration tip to the aspiration position; and
a cooling housing that holds a specimen rack for storing an aspirated tip after aspiration and that cools the tip.

2. The cell aspiration support system according to claim 1, wherein the cooling housing comprises
a cooler that uses a Peltier element, and
a heat transfer member that contacts with the cooler and that includes holes for receiving tip ends of aspirated tips.

3. The cell aspiration support system according to claim 2, wherein
the heat transfer member contacts with a cooling side of the cooler, and
the cooling housing further comprises a heat sink provided on a heat exhaust side of the cooler.

4. The cell aspiration support system according to claim 2, wherein the cooling housing comprises a heat insulation member that surrounds the cooler and the heat transfer member.

5. The cell aspiration support system according to claim 1, wherein the cooling housing comprises
an opening-and-closing type heat insulation cover that is opened when the aspirated tip after aspiration is stored in the specimen rack.

6. The cell aspiration support system according to claim 5, wherein
the opening-and-closing type heat insulation cover opens and closes along with movement of the aspiration tip.

7. The cell aspiration support system according to claim 1, wherein
the cooling housing surrounds the specimen rack.

* * * * *